(12) United States Patent
Foody et al.

(10) Patent No.: US 8,017,820 B2
(45) Date of Patent: Sep. 13, 2011

(54) CONTINUOUS FLOWING PRE-TREATMENT SYSTEM WITH STEAM RECOVERY

(75) Inventors: Brian Foody, Ottawa (CA); Vijay Anand, Brossard (CA); David Rea, Manotick (CA)

(73) Assignee: Iogen Energy Corporation, Ontario (CA)

( * ) Notice: Subject to any disclaimer, the term of this patent is extended or adjusted under 35 U.S.C. 154(b) by 1124 days.

(21) Appl. No.: 10/592,906

(22) PCT Filed: Sep. 30, 2005

(86) PCT No.: PCT/CA2005/001493
§ 371 (c)(1),
(2), (4) Date: Jun. 15, 2007

(87) PCT Pub. No.: WO2006/034590
PCT Pub. Date: Apr. 6, 2006

(65) Prior Publication Data
US 2008/0064906 A1 Mar. 13, 2008

(51) Int. Cl.
*C10G 1/00* (2006.01)
*D21C 3/26* (2006.01)

(52) U.S. Cl. ............ 585/242; 585/240; 162/17; 162/22; 162/243

(58) Field of Classification Search .................. 585/240, 585/242; 127/1, 2, 9; 162/17, 22, 243, 173
See application file for complete search history.

(56) References Cited

U.S. PATENT DOCUMENTS

| 2,108,567 A | 2/1938 | Scholler et al. |
| 2,681,871 A | 6/1954 | Wallace et al. |
| 3,212,932 A | 10/1965 | Hess et al. |

(Continued)

FOREIGN PATENT DOCUMENTS
EP  1 316 620 A2  6/2003

OTHER PUBLICATIONS

Ghose, T.K., "Measurement of Cellulase Activities," Pure & Appl. Chem. 59:257-268 (1987).

(Continued)

*Primary Examiner* — Nina Bhat
(74) *Attorney, Agent, or Firm* — Fitzpatrick, Cella, Harper & Scinto

(57) ABSTRACT

The present invention is directed to a continuous process for pretreating a lignocellulosic feedstock. A feedstock slurry is provided, which has a solids concentration of 10% to 33% by weight. The feedstock slurry is pumped through a heating train of at least two stages, each stage including a pump to increase stage pressure and a direct steam injection to heat the feedstock slurry. Acid is also added to the feedstock slurry prior to the heating train, during a heating stage, or after leaving the heating train; the acid is added at a concentration of 0% to 12% weight of acid on weight of initial feedstock. A heated, acidified feedstock slurry is thus produced. The heated, acidified feedstock slurry is flowed through a pretreatment reactor at a temperature of 160° C. to 280° C. for a time sufficient to increase efficiency of conversion of cellulose in the feedstock to glucose using cellulase enzymes. After the slurry exits the pre-treatment reactor, it is cooled using two, or more than two flashing stages at successively lower pressures, without intermittent increases in pressure. The steam energy, at or near its flash temperature, from two or more than two of the flashing stages is used to heat the feedstock slurry in the heating train.

18 Claims, 1 Drawing Sheet

U.S. PATENT DOCUMENTS

| | | | |
|---|---|---|---|
| 4,136,207 A | 1/1979 | Bender | |
| 4,137,094 A | 1/1979 | Hughes | |
| 4,237,226 A | 12/1980 | Grethlein | |
| 4,316,747 A | 2/1982 | Rugg et al. | |
| 4,316,748 A * | 2/1982 | Rugg et al. | 127/37 |
| 4,318,748 A | 3/1982 | Church | |
| 4,427,453 A | 1/1984 | Reitter | |
| 4,461,648 A | 7/1984 | Foody | |
| 4,468,256 A | 8/1984 | Hinger | |
| 4,478,644 A * | 10/1984 | Berger et al. | 127/1 |
| 4,556,430 A | 12/1985 | Converse et al. | |
| 4,591,386 A * | 5/1986 | Rugg et al. | 127/1 |
| 4,615,742 A | 10/1986 | Wright | |
| 5,089,086 A | 2/1992 | Silander | |
| 5,114,488 A * | 5/1992 | Huber et al. | 127/1 |
| 5,188,673 A * | 2/1993 | Clausen et al. | 127/37 |
| 5,366,558 A | 11/1994 | Brink | |
| 5,411,594 A * | 5/1995 | Brelsford | 127/37 |
| 5,628,830 A | 5/1997 | Brink | |
| 6,063,204 A * | 5/2000 | Hester et al. | 127/1 |
| 6,176,971 B1 | 1/2001 | Sun Yu et al. | |
| 6,179,958 B1 | 1/2001 | Lysen et al. | |
| 6,306,252 B1 | 10/2001 | Ryham | |
| 6,346,166 B1 | 2/2002 | Kettunen et al. | |
| 6,419,788 B1 | 7/2002 | Wingerson | |
| 6,620,292 B2 | 9/2003 | Wingerson | |
| 6,722,130 B1 | 4/2004 | Snekkenes et al. | |
| 7,238,242 B2 * | 7/2007 | Pinatti et al. | 127/37 |
| 7,815,876 B2 * | 10/2010 | Olson | 422/232 |

OTHER PUBLICATIONS

Grethlein, H.E., "Chemical Breakdown of Cellulosic Materials," J. Appl. Chem. Biotechnol. 28:296-308 (1978).

Teleman, A., et al., "Progress-curve analysis shows that glucose inhibits the cellotriose hydrolysis catalysed by cellobiohydrolase II . . . ," Eur. J. Biochem 231:250-258 (1995).

* cited by examiner

CONTINUOUS FLOWING PRE-TREATMENT SYSTEM WITH STEAM RECOVERY

The present invention relates to a pre-treatment process in the conversion of lignocellulosic feedstocks into products. More specifically, the present invention relates to a continuously flowing pre-treatment process with simultaneous steam recovery, for the conversion of lignocellulosic feedstocks into products.

BACKGROUND OF THE INVENTION

Fuel ethanol is currently produced from feedstocks such as cornstarch, sugar cane, and sugar beets. However, the production of ethanol from these sources cannot expand much further due to limited farmland suitable for the production of such crops and competing interests with the human and animal food chain. Finally, the use of fossil fuels, with the associated release of carbon dioxide and other products, in the conversion process is a negative environmental impact of the use of these feedstocks The possibility of producing ethanol from cellulose-containing feedstocks such as agricultural wastes, grasses, and forestry wastes has received much attention due to the availability of large amounts of these inexpensive feedstocks, the desirability to avoid burning or landfilling cellulosic waste materials, and the cleanliness of ethanol as a fuel compared to gasoline. In addition, a byproduct of the cellulose conversion process, lignin, can be used as a fuel to power the cellulose conversion process, thereby avoiding the use of fossil fuels. Studies have shown that, taking the entire cycle into account, the use of ethanol produced from cellulose generates close to nil greenhouse gases.

The cellulosic feedstocks that may be used for ethanol production include (1) agricultural wastes such as corn stover, wheat straw, barley straw, canola straw, oat straw, and soybean stover; (2) grasses such as switch grass, miscanthus, cord grass, and reed canary grass, (3) forestry wastes such as aspen wood and sawdust, and (4) sugar processing residues such as bagasse and beet pulp.

Cellulose consists of a crystalline structure that is very resistant to breakdown, as is hemicellulose, the second most prevalent component. The conversion of cellulosic fibers to ethanol requires: 1) liberating cellulose and hemicellulose from lignin or increasing the accessibility of cellulose and hemicellulose within the cellulosic feedstock to cellulase enzymes, 2) depolymerizing hemicellulose and cellulose carbohydrate polymers to free sugars and, 3) fermenting the mixed hexose and pentose sugars to ethanol.

Among well-known methods used to convert cellulose to sugars is an acid hydrolysis process involving the use of steam and acid at a temperature, acid concentration and length of time sufficient to hydrolyze the cellulose to glucose (Grethlein, 1978, J. Appl. Chem. Biotechnol. 28:296-308). The glucose product is then fermented to ethanol using yeast, and the ethanol is recovered and purified by distillation.

An alternative method of cellulose hydrolysis is an acid prehydrolysis (or pre-treatment) followed by enzymatic hydrolysis. In this sequence, the cellullosic material is first pre-treated using the acid hydrolysis process described above, but at milder temperatures, acid concentration and treatment time. This pre-treatment process is thought to increase the accessibility of cellulose within the cellulosic fibers for subsequent enzymatic conversion steps, but results in little conversion of the cellulose to glucose itself. In the next step, the pre-treated feedstock is adjusted to an appropriate temperature and pH, then submitted to enzymatic conversion by cellulase enzymes.

The hydrolysis of the cellulose, whether by acid or by cellulase enzymes, is followed by the fermentation of the sugar to ethanol, which is then recovered by distillation.

The temperatures typically used for acid hydrolysis or pre-treatment correspond to saturated steam pressures of 160 psig to 665 psig. The addition of sulphuric acid improves the digestion of the cellulose and shortens the time for pre-treatment from 5-30 minutes to 0.1-5 minutes. Achieving and maintaining these conditions requires a highly pressurized, acid-resistant system. U.S. Pat. No. 4,416,648 (Foody) describes equipment and conditions used in steam explosion pre-treatment, in which the feedstock, steam, and sulfuric acid are added to a reaction vessel, known as a steam gun. In the steam gun, steam is added and the steam pressure is increased rapidly to the desired pressure, followed by sudden explosive decompression. Steam explosion with sulfuric acid added has been the standard pre-treatment process for two decades. It produces pre-treated material that is uniform, has most of the hemicellulose hydrolyzed to simple sugar, and less cellulase enzyme is subsequently required to hydrolyze the cellulose than other pre-treatment processes.

Although steam explosion and other batch pre-treatment processes prepare feedstocks with highly accessible cellulose, they have inherently low throughput. This requires the use of many steam pre-treatment reactors, which is costly and difficult to operate. Furthermore, it is difficult in batch processes—and in steam explosion in particular—to recover and reuse the steam. The steam requirement to achieve and maintain the feedstock at acid hydrolysis or pre-treatment conditions is high. The loss of this steam after a single treatment represents a significant cost in the ethanol production process.

The development of a continuous pre-treatment process delivering the degree of accessibility of the cellulose from a steam explosion process, and that can be economically operated and maintained, has been the focus of a significant research in the field.

U.S. Pat. No. 4,136,207 (Bender) teaches steam pre-treatment to produce a ruminant feed. The feedstock is saturated with moisture and compacted at 2000 psi to remove air and improve the subsequent penetration of steam. A rotating helical feed screw conveys the compacted feedstock into a barrel. Steam made from a steam generator is fed into the reactor barrel at 200-310 psi. The feedstock proceeds through the barrel, at the end of which is a valve to allow steam and volatiles to escape, and a product valve for treated solids to exit. Steam, which is collected in a byproduct recovery column, is returned to the reactor barrel. However, this process does not allow for dilute acid pre-soaking or leaching of the feedstock, nor does the low moisture content of the feedstock allow for pumping of the feedstock. Furthermore, this process does not provide for the use of sulphuric acid, which is required for rapid reaction and the production of maximum accessibility of the cellulose. The absence of sulphuric acid decreases the quality of the pre-treated material, and requires a pre-treatment reactor of increased size. The nature of the pre-treatment reactor used by Bender may inhibit uniform penetration of steam into the fibers due to the formation of pucks and slivers in the material. In addition, adequate sealing of the high-pressure vessel is a challenge.

U.S. Pat. No. 5,366,558 (Brink) describes a continuous acid hydrolysis process that occurs in several stages. The first stage is a steam treatment in the absence of acid. The material is then mechanically disintegrated to a very small particle size, acidified, and sensitized with oxygen. The sensitized material is then heated with steam for the final hydrolysis reaction. The material is washed countercurrently, with the sugar stream and lignin being the products. As multiple reaction steps at high temperature and pressure are required, the risk of severe degradation of the feedstock increases. This in turn limits the level of cellulose conversion and, thereby, the commercial viability of the process. There is no teaching of steam recovery.

U.S. Pat. No. 5,628,830 (Brink) teaches a steam pre-treatment followed by multiple flashes for steam recovery. The lignocellulosic material is finely ground, subjected to a first acid hydrolysis (pre-treatment) stage, then passed through a disintegrator. The slurry then undergoes multiple flashing stages, with steam being recycled, followed by simultaneous saccharification and fermentation to yield ethanol. However, the feedstock of Brink has a moisture content that is too low to allow pumping of the material, and prevents pre-soaking of the feedstock in dilute acid or leaching of the feedstock. In addition, the pre-treatment method of Brink requires the addition of acid at a point where the acid is present through several pieces of equipment; this in turn requires that each piece of equipment be resistant to acid, which adds considerable expense. Finally, the method of '830 recovers and reuses only a portion of the steam, falling short of recovering the substantial amount of steam required for a cost-effective pre-treatment operation.

U.S. Pat. No. 4,237,226 (Grethlein) teaches a continuous pre-treatment in which cellulosic material is slurried in water to about 5-10% solids. The slurry is heated to the reaction temperature and a concentrated stream of sulfuric acid is injected. The acidified slurry is then heated by the injection of live steam to allow for very rapid heating of the slurry. Rapid cooling quenches of the reaction, by flashing across an orifice or capillary at the outlet to the reactor is described. However, recovery of steam is not described.

U.S. Pat. No. 4,556,430 (Converse) includes a non-aqueous carrier in the feedstock to decrease the amount of water present. However, the carrier must be recovered. As some of the lignin may be dissolved by the carrier, recovery of the lignin and carrier is complex. Furthermore, there is no teaching of steam recovery.

U.S. Pat. No. 4,468,256 (Hinger) discloses a process for the hydrolysis of cellulose in vegetable raw materials. The raw material is comminuted and impregnated with dilute acid, after which excess moisture is removed from the material. The acidified material is preheated using recycled steam and is then fed into a reactor, where it is heated in a heating zone. High pressure steam is injected into the material in a hydrolysis zone. The material is subsequently cooled in a release zone, where pressure is rapidly released; the released steam is recycled to the heating zone. Residual steam remaining in the treated materials exits through a port and is recycled to the initial preheating stage. However, the method of Hinger requires the addition of acid at a point where the acid is present through several pieces of equipment, which requires that each piece of equipment be resistant to acid, adding considerable expense. Further, the feedstock of Hinger has a moisture content that is too low to allow pumping of the acidified material.

At present, methods of improved feedstock pre-treatment prior to enzymatic hydrolysis are not particularly economic. More specifically, known methods often require that several pieces of equipment be resistant to acid, which increases equipment costs. Also, many methods require a high steam usage to heat the water of slurried feedstocks. Others do not use slurried feedstocks, but rather dried or compacted materials that cannot be pumped.

SUMMARY OF THE INVENTION

The present invention relates to a pre-treatment process in the conversion of lignoceuulosic feedstocks into products. More specifically, the present invention relates to a continuously flowing pre-treatment process with simultaneous steam recovery, for the conversion of lignocellulosic feedstocks into products.

It is an object of the present invention to provide a continuous flowing pre-treatment system with steam recovery. Preferably, the pre-treatment system operates at reduced cost when compared to currently available methods.

The present invention provides a continuous process for pre-treating a lignocellulosic feedstock, comprising:
(a) providing a feedstock slurry having a solids concentration of 8% to 30% by weight;
(b) pumping the feedstock slurry through a heating train of two, or more than two stages, each stage including a pump to increase stage pressure and a direct steam injection to heat the feedstock slurry, and adding acid to the feedstock slurry prior to the heating train, during a heating stage, or after leaving the heating train, the acid added at a concentration of 0% to 12% weight of acid on weight of initial feedstock, to produce a heated, acidified feedstock slurry;
(c) flowing the heated, acidified feedstock slurry through a pre-treatment reactor at a temperature of 160° C. to 280° C. for a time sufficient to increase efficiency of conversion of cellulose in the feedstock to glucose using cellulase enzymes;
(d) after the slurry exits the pre-treatment reactor, cooling the slurry using two, or more than two flashing stages at successively lower pressures, without intermittent increases in pressure;
(e) using steam energy from two or more than two of the flashing stages, at or near its flash temperature, to heat the feedstock slurry in the heating train.

The present invention also provides the process defined above, wherein the feedstock is agricultural wastes such as corn stover, wheat straw, oat straw, barley straw, canola straw, and soybean stover; grasses such as switch grass, miscanthus, cord grass, and reed canary grass; or any combination thereof.

The present invention pertains to the process defined above, wherein the feedstock is slurried in water. The present invention is also directed to the method as just described, wherein the heating train consists of 2 to 8 stages. Furthermore, the step of cooling (step (c)) as just described may comprise 2 to 8 flashing stages. This configuration of the present invention may cool the slurry to a temperature of about 30° C. to about 70° C. after a final flashing stage.

The present invention pertains to the process described above, wherein the acid is sulphuric acid, sulfurous acid, or sulfur dioxide.

The present invention is also directed to the method as just described, wherein the acid is added to the feedstock slurry prior to the heating train. Alternatively, the acid may be added to the feedstock slurry after the heating train, or may be added to the feedstock slurry in a final heating stage.

The present invention pertains to the process defined above, wherein the feedstock is reacted at a temperature of less than about 170° C. in the present of about 0.5% to about 3% sulfuric acid to hydrolyze the hemicellulose prior to the step of flowing (step (c)).

The present invention is also directed to the method as described above, wherein the slurry is submitted to enzymatic hydrolysis subsequent to the step of cooling (step d).

The process of the present invention overcomes the disadvantages of the prior art by using multiple heating stages corresponding to the temperatures of the steam streams that are available. Steam at various pressures is obtained in the flashing stages, where it is captured and used in downstream processing, or to heat the feedstock in the heating stages. In addition to avoiding the inefficiencies associated with increases and decreases in steam pressure in the flash train, this process also avoids the expense of multiple pumps and nozzles in the flashing stages. Furthermore, additional heating costs are avoided, as the feedstock is slurried in liquid at a solids concentration low enough to be pumped, but without adding excess liquid. Also, the addition of acid to the feedstock at selected locations minimizes the contact of acid with the equipment.

The method of the present invention improves the overall economics of the pre-treatment process. The contact between concentrated acid and the process equipment is minimized, thereby saving in capital and maintenance costs. The second stage pH is high enough to protect the metallurgy of the downstream process equipment, which is threatened by the pre-treatment pH. Furthermore, the present invention permits flashing to recover steam and volatiles while improving the stability of the sugar. Also, the tendency of lignin, salts and other compounds to precipitate is decreased. In addition, the method of the present invention is amenable to the pre-treatment of straw, grass, and other agricultural feedstocks.

Therefore, the invention offers significant advances in the pre-treatment of lignocellulosic feedstock.

This summary of the invention does not necessarily describe all necessary features of the invention.

BRIEF DESCRIPTION OF THE DRAWINGS

These and other features of the invention will become more apparent from the following description in which reference is made to the appended drawings wherein.

DESCRIPTION OF PREFERRED EMBODIMENT

Figure 1:
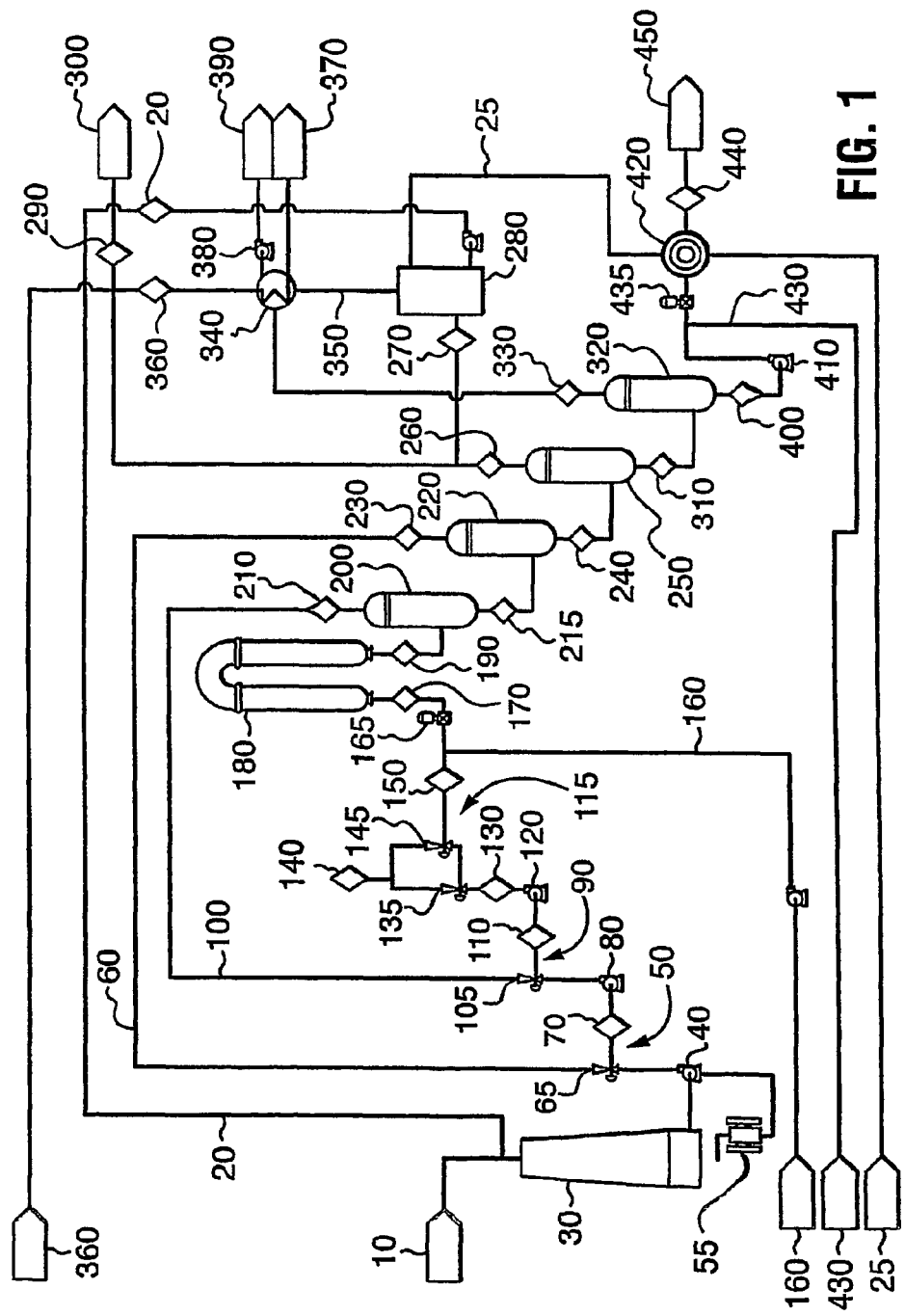
FIG. 1 shows a schematic diagram of the process of a continuous flowing pre-treatment process according to the present invention.

The present invention relates to a pre-treatment process in the conversion of lignocellulosic feedstocks into products. More specifically, the present invention relates to a continuously flowing pre-treatment process with simultaneous steam recovery, for the conversion of lignocellulosic feedstocks into products.

The following description is of a preferred embodiment by way of example only and without limitation to the combination of features necessary for carrying the invention into effect.

The present invention provides a continuous pre-treatment process of lignocellulosic feedstocks that involves preheating a pumpable feedstock slurry using two or more than two successive heating stages. Each stage is at a higher temperature than the previous stage. The higher temperatures are successively achieved by recycling flash steam from the pre-treatment process. The final heat-up of the feedstock prior to the pre-treatment reactor is by injection of live steam. Acid is also added to the feedstock, and the heated, acidified feedstock is held in a pre-treatment reactor for a time sufficient to improve the efficiency of the hydrolysis of cellulose in the feedstock by cellulase enzymes. The pre-treated material is then subjected to two or more than two successive flashing stages to cool down the contents and to remove the steam for reuse. There is no intermittent increase in steam temperature or pressure in the flashing stages. The flashed steam is captured and sent to the heating stages to be used with minimal loss of pressure, ensuring efficient recovery of the steam.

According to an embodiment of the present invention there is provided a continuous process for pre-treating a lignocellulosic feedstock, comprising:

(a) providing a feedstock slurry having a solids concentration of 8% to 30% by weight;

(b) pumping the feedstock slurry through a heating train of two, or more than two heating stages, each heating stage including a pump to increase stage pressure and a direct steam injection to heat the feedstock slurry;

(c) adding acid to the feedstock slurry prior to the heating train, during a heating stage, or after leaving the heating train, the acid added at a concentration of 0% to 12% weight of acid on weight of initial feedstock, to produce a heated, acidified feedstock slurry;

(d) flowing the heated, acidified feedstock slurry through a pre-treatment reactor at a temperature of 160° C. to 280° C. for a time sufficient to increase efficiency of conversion of cellulose in the feedstock to glucose using cellulase enzymes;

(e) after the slurry exits the pre-treatment reactor, cooling the slurry using two, or more than two flashing stages at successively lower pressures, without intermittent increases in pressure;

(f) using steam energy from two or more than two of the flashing stages, at or near its flash temperature, to heat the feedstock slurry in the heating train.

By "continuous process", it is meant a process that involves continuous feeding of feedstock and withdrawal of pre-treated feedstock.

By the term "lignocellulosic feedstock", "lignocellulosic material" or "lignocellulosic substrate" it is meant any type of biomass comprising cellulose such as, but not limited to non-woody plant biomass, agricultural wastes and forestry residues and sugar-processing residues. Generally, a lignocellulosic material is recognized as containing cellulose in an amount greater than about 20% (w/w), about 15% or more hemicellulose, and about 15% lignin. The cellulosic material can be of higher cellulose content, for example at least about 30% (w/w), 35% (w/w), 40% (w/w) or more. For example, the cellulosic material may comprise from about 20% to about 50% (w/w) cellulose, or more, or any amount therebetween, for example but not limited to 20, 22, 24, 26, 28, 30, 32, 34, 36, 38, 40, 42, 44, 46, 48, and 50% (w/w) cellulose.

In a non-limiting example, the lignocellulosic feedstock can include, but is not limited to grasses, such as switch grass, cord grass, rye grass, reed canary grass, miscanthus, or a combination thereof; sugar-processing residues such as, but not limited to sugar cane bagasse; agricultural wastes such as, but not limited to rice straw, rice hulls, corn cobs, barley straw, wheat straw, canola straw, oat straw, oat hulls, and corn fiber; stover, such as, but not limited to soybean stover, corn stover; and forestry wastes, such as, but not limited to recycled wood pulp fiber, sawdust, hardwood, softwood, or any combination thereof. Lignocellulosic feedstock may comprise one species of fiber, or alternatively lignocellulosic feedstock may comprise a mixture of fibers that originate from different lignocellulosic feedstocks. Agricultural wastes such as wheat straw, oat straw, barley straw, and canola straw; stovers such as corn stover and soybean stover; grasses such as switch grass, reed canary grass, cord grass, and miscanthus; or combinations thereof are particularly advantageous as lignocellulosic feedstocks, due to their widespread availability and low cost.

The present invention may be practiced with lignocellulosic feedstock that has been subjected to size reduction. Size reduction by any suitable mechanical action is acceptable, including grinding, milling, agitation, shredding, compression/expansion, or other types of mechanical action. Mechanical action can-be performed by any type of equipment adapted for the purpose, for example but not limited to a hammer mill. Feedstock size may be reduced to particles of size of about 20 to about 60 mesh, or any amount therebetween; for example the particle size may be about 20, 25, 30, 35, 40, 45, 50, 55, or 60 mesh. Chemical action typically includes the use of heat (often steam), acid, and solvents. Several chemical and mechanical pre-treatment methods are well known in the art.

The lignocellulosic material is slurried in liquid to a solids content of about 8% to about 30% (w/w) suspended (undissolved) solids, or any amount therebetween; for example, the feedstock slurry may be about 10, 12, 15, 18, 20, 22, 25, 28, 30% (w/w) suspended solids, or any amount therebetween. The liquid may be any suitable liquid known in the art. For example, but without wishing to be limiting the liquid may be water, an organic liquid that is miscible or immiscible in water, or a combination thereof. The use of organic liquids in pre-treatment systems is described by U.S. Pat. No. 4,556,430 (which is incorporated herein by reference), and has the advantage that the low boiling point liquid can be recovered and reused. Other pretreatment processes, such as the ORGANOSOLV™ process, also use organic liquids. In the case where an organic liquid is used to slurry the feedstock, the liquid may be recovered in the flashing step and recycled to the slurry point or the heating train for reuse.

In a non-limiting example, the feedstock is slurried in water. The water can be recirculated from elsewhere in the process, may be heated immediately prior to addition to the feedstock, or a combination thereof. The amount water added makes pumping of the feedstock possible, particularly with a medium consistency (MC) pump, or other pump suitable for handling medium-consistency slurry. The optimum amount of water depends on the physical properties of the feedstock, and can be determined by methods well known to a person of skill in the art. Excess quantities of water will result in additional heat requirements and reduce efficiency of the process, while quantities that are too small will be absorbed by the feedstock and impact pumpability.

The liquid used to slurry the feedstock may be at a temperature of about 40° C. to about 90° C., or any temperature therebetween; for example, the feedstock may be at about 40, 45, 50, 55, 60, 65, 70, 75, 80, 85, or 90° C., or any temperature therebetween. The hot liquid may be recirculated from elsewhere in the process, or heated immediately prior to addition to the feedstock. The feedstock and the liquid can be combined in a soaking tank, a drop leg toward a tank, or by any other suitable means.

The slurried feedstock then enters the heating train. By the term "heating train", it is meant two or more than two stages of steam heating of the slurried feedstock, each stage at successively higher temperatures. The number of stages in a heating train should be high enough to provide the ability to use steam at the different pressures that are available, but low enough so the cost of pumps and the complexity is reasonable. In a non-limiting example, about 2 to about 8 stages, or any amount therebetween, may be used; for example, a heating train may have about 2, 3, 4, 5, 6, 7 or 8 stages. In each stage, the steam may be directly injected into each heating stage using steam mixers, which will be familiar to those of skill in the art (see Pulp Bleaching: Principles and Practice, Reeve and Dence, p. 539-568, which is incorporated herein by reference). This method results in a rapid, uniform heating of the slurry, thereby minimizing degradation of the feedstock.

The final heating stage may involve the injection of live steam immediately prior to the pre-treatment reactor. The steam pressure in the final stage is the pressure at which the saturated steam corresponds to the pre-treatment temperature. The pre-treatment temperature will generally depend on the retention time, acid concentration, feedstock used and degree of treatment required; the pre-treatment temperature is generally between about 160° C. and about 280° C., or any temperature therebetween. For example, the temperature may be about 160, 170, 175, 180, 185, 190, 195, 200, 205, 210, 215, 220, 225, 230, 235, 240, 245, 250, 255, 260, 265, 270, 275, or 280° C. It will be understood by those of skill in the art that the condensation of steam in the slurry decreases the solids concentration to about 80% of its initial value. For example, the concentration of the slurry entering the pre-treatment reactor is about 8% to about 26% feedstock solids.

Acid is added to the feedstock slurry, either prior to the heating train, during a heating stage, or after leaving the heating train. For example, but without wishing to be limiting in any manner, the acid may be added in the final heating stage. In this case, the acid may be added immediately prior to, or immediately after the point of live steam injection. If the acid is added prior to entry into the heating train, the metallurgy of the system should be adapted to handle acidic conditions. The acid is added in a manner that allows it to mix into the slurry. For example, the acid may be diluted with water to a concentration of about 10% using a mixing tee, then added directly to the feedstock slurry. It is particularly advantageous to add the acid as close to the pre-treatment reactor as possible, as this will minimize the amount of equipment that is exposed to potential corrosion.

Any suitable acid may be used in the process of the present invention. For example, sulphuric acid, sulphurous acid, sulfur dioxide, or combinations thereof can be used. In a specific non-limiting example, sulphuric acid, which is inexpensive, water soluble at high concentrations, stable, non-volatile, and capable of catalyzing the reactions desired in pre-treatment, is used. The acid may be provided in a 93% concentrate. The amount of acid added may vary, but should be sufficient to achieve a final concentration of acid of about 0% to about 12% w/w, or any amount therebetween, of feedstock solids. The resulting pH of the slurry should be within the range of about 0.8 to about 2.0 or any pH therebetween. For example, the pH of the slurry may be between about 0.8, 0.9, 1.0, 1.1, 1.2, 1.3, 1.4, 1.5, 1.6, 1.7, 1.8, 1.9, or 2.0.

The pre-treatment reactor is designed to maintain a plug flow of the slurry and may be constructed of any suitable material resistant to corrosion and erosion at reaction conditions. For example, but without wishing to be limiting, the reactor may be constructed of zirconium, tantalum, nionium, ceramic tiles, or other such resistant materials. A valve or orifice at the exit of the reactor maintains the back pressure necessary for maintenance of the steam pressure at a desired level.

The retention time in the pre-treatment reactor will vary depending on temperature, acid concentration, feedstock used, and the degree of treatment desired. For example, the slurry could be retained in the reactor for about 0.05 to about 10 minutes, or any time therebetween; for example, the retention time can be about 0.05, 0.1, 0.5, 1, 1.5, 2, 2.5, 3, 3.5, 4, 4.5, 5, 5.5, 6, 6.5, 7, 7.5, 8, 8.5, 9, 9.5, or 10 minutes.

Upon exiting the pre-treatment reactor, the slurry is subjected to two or more than two flashing stages to cool the material, and to remove steam and volatiles from the system.

For example, about 3 to about 8 successive flashing stages, or any amount therebetween, can be performed; for example, there may be about 3, 4, 5, 6, 7, or 8 flashing stages. The multiple flashing stages generate flash steam at different pressures. This permits multiple uses of the steam, contributing to the overall process economics. In this manner, the energy of the steam is used multiple times, as the steam can be used directly or indirectly, by heating a process stream.

The flash steam may be sent to the heating train for heating the feedstock prior to pre-treatment, entering the heating train at a stage having a similar temperature as the recycled steam. In a non-limiting example, there is no intermittent increase in pressure between flashes, thus avoiding the inefficiency of raising and lowering steam pressure.

Alternatively, the flashed steam may be used to heat a second stream of water, steam, or a combination thereof, and this second stream may then be sent to the heating train. This also leads to an efficient use of the steam. Furthermore, the steam from some flash stages can be used as a source of low pressure steam in the plant. This is a particularly attractive option for the low pressure steam from the later flash stages. However, the steam from two, or more than two flash stages is used, directly or indirectly, in the heating train.

Once the flashed slurry has been cooled to a temperature of about 50° C. to about 100° C., or any temperature therebetween, the pH of the slurry is adjusted to a pH in the range compatible with subsequent enzymatic hydrolysis. For example the temperature of the slurry may be about 50, 55, 60, 65, 70, 75, 80, 85, 90, 95, or 100° C. Generally, the pH of the slurry is adjusted to about 4.5 to about 5.5, or any pH therebetween, using a suitable alkaline solution; for example, the pH may be adjusted to about 4.5, 4.6, 4.7, 4.8, 4.9, 5.0, 5.1, 5.2, 5.3, 5.4, or 5.5. However, the pH of the slurry can be higher or lower than about 4.5 to 5.5 if the cellulase enzymes used are alkalophilic or acidophilic, respectively. It remains that the pH of the slurry should be adjusted to within the range of optimum pH for the enzymes used. For pH adjustments, any suitable alkaline solution known in the art can be used, for example, but not limited to sodium hydroxide, potassium hydroxide, ammonium hydroxide, ammonia, or calcium hydroxide.

The slurry may also be cooled to the optimum temperature for enzymatic hydrolysis, which may be done using a heat exchanger. The heat exchanger cools the slurry to about 30° C. to about 70° C., the temperature range depending on the cellulase enzymes used. Generally, a temperature in the range of about 45° C. to about 55° C., or any temperature therebetween is suitable for most cellulase enzymes; for example, the temperature may be about 45, 46, 47, 48, 49, 50, 51, 52, 53, 54, or 55° C. However, the temperature of the slurry may be higher for thermophilic cellulase enzymes. For example, but without wishing to be limiting, the slurry is cooled to about 50° C. for hydrolysis performed with cellulase enzymes. A none limiting example of a cellulase enzyme mixture may be made by the fungus *Trichoderma*.

By the term "cellulase enzymes", "cellulase", or "enzymes", it is meant enzymes that catalyse the hydrolysis of cellulose to products such as glucose, cellobiose, and other cellooligosaccharides. Cellulase is a generic term denoting a multienzymne mixture comprising exo-cellobiohydrolases (CBH), endoglucanases (EG) and β-glucosidases (βG) that can be produced by a number of plants and microorganisms. The process of the present invention can be carried out with any type of cellulase enzymes, regardless of their source. Among the most widely studied, characterized, and commercially produced cellulases are those obtained from fungi of the genera *Aspergillus, Humicola,* and *Trichoderma,* and from the bacteria of the genera *Bacillus* and *Thermobifida*. Cellulase produced by the filamentous fungi *Trichoderma longibrachiatum* comprises at least two cellobiohydrolase enzymes termed CBHI and CBHII and at least 4 EG enzymes.

Cellulase enzymes work synergistically to degrade cellulose to glucose. CBHI and CBHII generally act on the ends of the glucose polymers in cellulose microfibrils liberating cellobiose (Teeri and Koivula, 1995, Carbohydr. Europe 12, 28-33) while the endoglucanases act at random locations on the cellulose. Together these enzymes hydrolyse cellulose to smaller cello-oligosaccharides such as cellobiose. Cellobiose is hydrolysed to glucose by β-glucosidase.

The cellulase enzyme dosage added to the slurry is chosen to achieve a sufficiently high level of cellulose conversion. For example, an appropriate cellulase dosage can be about 5.0 to about 50.0 Filter Paper Units (FPU or IU) per gram of cellulose, or any amount therebetween. For example, the cellulase dosage may be about 5, 8, 10, 12, 15, 18, 20, 22, 25, 28, 30, 32, 35, 38, 40, 42, 45, 48, or 50 FPU, or any amount therebetween. The FPU is a standard measurement familiar to those skilled in the art and is defined and measured according to Ghose (1987, Pure and Appl. Chem. 59:257-268). An adequate quantity of β-glucosidase (cellobiase) activity is also added to the mixture. The dosage level of β-glucosidase may be about 5 to about 400 β-glucosidase units per gram of cellulose, or any amount therebetween, or from about 35 to about 100 β-glucosidase units per gram of cellulose; for example, the dosage may be 35, 40, 45, 50, 55, 60, 65, 70, 75, 80, 85, 90, 95, 100, 125, 150, 175, 200, 225, 250, 275, 300, 325, 350, 375, or 400 β-glucosidase units per gram of cellulose, or any amount therebetween. The β-glucosidase unit is measured according to the method of Ghose (1987, Pure and Appl. Chem. 59:257-268).

The enzymatic hydrolysis continues for about 24 to about 250 hours, or any amount of time therebetween, depending on the degree of conversion desired. For example, the reaction time could be about 24, 30, 40, 50, 60, 70, 80, 90, 100, 110, 120, 130, 140, or 150 hours, or any amount therebetween. The resulting slurry is an aqueous solution of glucose and xylose with lignin and other unconverted, suspended solids. The sugars are readily separated from the suspended solids and may be further processed as required, for example but not limited to fermentation to ethanol by yeast.

In another non-limiting example of the present invention, a two-stage pre-treatment system may be used. In the first stage, the acidified feedstock is heated in the heating train to a temperature below about 170° C. The feedstock is then reacted at about 170° C. in the present of about 0.5% to about 3% acid to hydrolyze the hemicellulose prior to the main pre-treatment reaction. The solubilized hemicellulose can optionally be washed away from the slurry with water, thereby preventing degradation of the sugar in the second stage of pre-treatment. The remaining feedstock is then submitted to the second stage of pre-treatment involving the conditions outlined above. For example, the second stage of pre-treatment may involve pumping the feedstock slurry through a heating train of two, or more than two heating stages, each heating stage including a pump to increase stage pressure and a direct steam injection to heat the feedstock slurry. Followed by adding acid to the feedstock slurry prior to the heating train, during a heating stage, or after leaving the heating train, the acid added at a concentration of 0% to 12% weight of acid on weight of initial feedstock, to produce a heated, acidified feedstock slurry. Then the heated, acidified feedstock slurry is passed through a pre-treatment reactor at a temperature of 160° C. to 280° C. for a time sufficient to increase efficiency of conversion of cellulose in the feedstock to glucose using cellulase enzymes. After the slurry exits the pre-treatment reactor, the slurry may then be cooled using two, or more than two flashing stages at successively lower pressures, without intermittent increases in pressure, and the steam energy from two or more than two of the flashing stages, at or near its flash temperature, may be used to heat the feedstock slurry in the heating train.

The present invention will be further illustrated in the following example. However, it is to be understood that these examples are for illustrative purposed only, and should not be used to limit the scope of the present invention in any manner.

EXAMPLE 1

With reference to FIG. 1, the feedstock 10, for example but not limited to wheat straw may be prepared by a shearing, crushing or a combination thereof operation, resulting in small particles at 54% moisture. About 70,000 kg/hr wheat straw (dry basis) may be slurried in 370,000 kg/hr water 20 at a temperature of about 93° C. in a drop leg (30) to reach a solids content of 14.4%.

The feedstock slurry is conveyed by pump 40 to the first stage of the heating train 50. Pump 40 may be a MC (medium consistency) pump with vacuum pump to handle the thick slurry. The heat to this stage is provided by direct injection of 32,200 kg/hr steam 60, for example at about 166° C. This injection heats the slurry to about 131° C.

The first stage slurry 70 is conveyed by pump 80 to the second stage of the heating train 90. Flash steam 100 at about 192° C. is injected at a rate of 37,300 kg/hr into this stream to heat the stream to about 168° C.

The heated slurry 110 is conveyed to the third heating stage by pump 120. The stream 130 is heated to about 196° C. and then about 220° C. with live steam at about 450 psig 140 added at about a rate of 32,000 kg/hr at each of two locations, to create stream 150. Stream 150 is at about 11% feedstock solids. At this point, sulfuric acid 160 is added to the slurry in an amount of about 4585 kg/hr to reach a concentration of about 6.55% acid by weight on initial feedstock solids to produce stream 170. Stream 170 is the feed stream for the pretreatment reactor 180.

The pre-treatment reactor 180 may be of any suitable configuration, for example a cylindrical pipe designed for a plug flow of the slurry. The inlet stream flows through the pre-treatment reactor 180 in approximately two minutes. This is sufficient to solubilize 95% of the hemicellulose, and 10% of the cellulose, with 12% degradation of the monomeric sugars. Upon exiting the pre-treatment reactor 180, the slurry 190 is flashed from about 368 psig to about 175 psig in the first flash tank 200. The flash steam and volatiles stream 210 is at a flow rate of about 37,300 kg/hr and may be used as the steam injection 100 in the second heating stage 90.

The slurry from the first flash tank 210 is at a flow rate of about 588,000 kg/hr and is flashed from about 175 psig to about 68 psig in a second flash tank 220. The steam and volatiles stream 230 is at a rate of about 32,200 kg/hr and is used to heat, via line 60, the first stage of the heating train 50.

The slurry from the second flash tank 240 is at a rate of about 555,600 kg/hr and is flashed from about 68 psig to about 45 psig in a third flash tank 250. About 20% of the volatile stream 260, which is about 8950 kg/hr at about 121° (270), is sent to an accumulator 280. The remaining 80% (290) which is about 37,200 kg/hr is used as a source of low pressure steam for the plant 300.

The slurry from the third flash tank 310 which is about 509,500 kg/hr is flashed from about 45 psig to about 6 psig in a fourth flash tank 320. The steam and volatiles stream 330 is at a flow rate of about 10,500 kg/hr at about 110° C. and is condensed at heat exchanger 340 and added to the accumulator 280 via line 350. The heat exchanger fluid is water stream 360 that flows out of the heat exchanger and is used as boiler feed water 370. Pump 380 is a vacuum pump that removes non-condensibles (390) from the flash stream.

The slurry stream from the fourth flash tank 400 is at a flow rate of about 499,000 kg/hr and a temperature of about 110° C. and is pumped by pump 410 to heat exchanger 420. Prior to the heat exchanger, ammonia 430 is injected into the slurry to adjust the pH up to 4.5 to 5.5. Process water stream 25 is the heat exchange fluid. The tempered water is added to the accumulator 280, where it is heated by streams 350 and the condensate from the third flash tank 270. The hot water from the accumulator 20 is used to slurry the feedstock in the initial drop leg 30. The cooled slurry 440 at about 70° C. is then cooled to about 50° C. and sent for enzymatic hydrolysis 450.

The method of the present invention improves the overall economics of the pre-treatment process. The contact between concentrated acid and the process equipment is minimized, thereby saving in capital and maintenance costs. The second stage pH is high enough to protect the metallurgy of the downstream process equipment, which is threatened by the pre-treatment pH. Furthermore, the present invention permits flashing to recover steam and volatiles while improving the stability of the sugar. Also, the tendency of lignin, salts and other compounds to precipitate is decreased. In addition, the method of the present invention is amenable to the pre-treatment of straw, grass, and other agricultural feedstocks.

The above description is not intended to limit the claimed invention in any manner. Furthermore, the discussed combination of features might not be absolutely necessary for the inventive solution.

We claim:

1. A continuous process for pre-treating a lignocellulosic feedstock, comprising:
    (a) providing a pumpable feedstock slurry having a solids concentration of 8% to 30% by weight;
    (b) pumping the feedstock slurry through a heating train of two, or more than two heating stages, each heating stage including a pump to increase heating stage pressure and a direct steam injection to heat the feedstock slurry;
    (c) adding acid to the feedstock slurry prior to the heating train, during a heating stage, or after leaving the heating train, the acid added at a concentration of 0.2% to 12% weight of acid on weight of initial feedstock, to produce a heated, acidified feedstock slurry;
    (d) flowing the heated, acidified feedstock slurry through a pre-treatment reactor at a temperature of 160° C. to 280° C. for a time sufficient to increase efficiency of conversion of cellulose in the feedstock to glucose using cellulase enzymes;
    (e) cooling the slurry after the slurry exits the pre-treatment reactor, using two, or more than two flashing stages at successively lower pressures, without increasing the steam pressure after flashing; and
    (f) using at least a portion of the steam energy from two or more than two of the flashing stages to heat the feedstock slurry in the heating train, wherein flash steam from at least one of the flashing stages, from which at least a portion of the flash steam is used in the heating train, has a pressure that is 20% to 99.5% of the inlet slurry pressure to such flashing stage.

2. The process of claim 1, wherein, in the step of providing (step a), the feedstock is selected from the group consisting of agricultural waste, grass, forestry biomass, sugar processing residues and combinations thereof.

3. The process of claim 2, wherein the agricultural waste is selected from the group consisting of corn stover, soybean stover, corn cobs, rice straw, rice hulls, corn fiber, wheat straw, barley straw, canola straw, oat straw, oat hulls and combinations thereof.

4. The process of claim 2, wherein the grass is selected from the group consisting of switch grass, miscanthus, cord grass, rye grass, reed canary grass and combinations thereof.

5. The process of claim 2, wherein the forestry biomass is selected from the group consisting of recycled wood pulp fiber, softwood, hardwood, sawdust and combinations thereof.

6. The process of claim 2, wherein the sugar processing residue is bagasse, beet pulp or combinations thereof.

7. The process of claim 1, wherein, in the step of providing (step a), the feedstock is slurried in an aqueous solution.

8. The process of claim 7, wherein, in the step of pumping (step b), the heating train comprises 2 to 8 heating stages.

9. The process of claim 8, wherein the step of cooling (step e) comprises 2 to 8 flashing stages.

10. The process of claim 9, wherein the slurry is subsequently cooled to about 30° C. to about 100° C. after the final flashing stage.

11. The process of claim 1, wherein, in the step of adding (step c), the acid is selected from the group consisting of sulfuric acid, sulfurous acid, and sulfur dioxide.

12. The process of claim 1, wherein, in the step of adding (step c), the acid is added to the feedstock slurry prior to the heating train.

13. The process of claim 1, wherein, in the step of adding (step c), the acid is added to the feedstock slurry after the heating train.

14. The process of claim 1, wherein, in the step of adding (step c), the acid is added to the feedstock slurry in a heating stage.

15. The process of claim 1, wherein, after the step of adding (step c) and before the step of pumping (step d), the feedstock slurry is reacted at a temperature of less than about 170° C. in the presence of about 0.5% to about 3% weight of acid on weight of initial feedstock to hydrolyze the hemicellulose.

16. The process of claim 1, wherein, after the step of cooling (step e), the slurry is submitted to enzymatic hydrolysis by cellulase enzymes.

17. The process of claim 1, wherein, in the step of pumping (step b), live steam is added to one or more than one heating stage to heat the feedstock slurry.

18. The process of claim 1, wherein, in the step of using steam energy (step f), flash steam, or a portion thereof, from at least one of the two or more flashing stages is used to heat a stream of water, steam, or a combination thereof, and wherein at least a portion of the heated stream is sent to the heating train to heat the feedstock slurry.

* * * * *